United States Patent [19]

Jones et al.

[11] Patent Number: 4,840,965
[45] Date of Patent: Jun. 20, 1989

[54] NAPHTHALENE ANTI-PSORIATIC AGENTS

[75] Inventors: Gordon H. Jones, Cupertino; Michael C. Venuti, San Francisco; John M. Young, Redwood City, all of Calif.

[73] Assignee: Syntex (U.S.A.) Inc., Palo Alto, Calif.

[21] Appl. No.: 70,456

[22] Filed: Jul. 7, 1987

[51] Int. Cl.⁴ ............... A01N 43/24; A01N 43/26; C07D 321/10; C07D 319/00

[52] U.S. Cl. .................... 514/450; 514/454; 514/463; 549/349; 549/359; 549/433

[58] Field of Search ............. 549/359, 349, 433; 514/454, 450, 463

[56] References Cited

U.S. PATENT DOCUMENTS

| | | | |
|---|---|---|---|
| 3,644,072 | 2/1987 | Vyas et al. | 549/433 |
| 4,229,478 | 10/1980 | Jones et al. | 424/331 |
| 4,466,981 | 8/1984 | Jones et al. | 424/311 |
| 4,500,542 | 2/1985 | Habicht et al. | 514/465 |
| 4,581,466 | 4/1986 | Morhold | 549/359 |

FOREIGN PATENT DOCUMENTS 565573 11/1944 United Kingdom.
1243401 8/1971 United Kingdom.

OTHER PUBLICATIONS

J. Chem. Soc., 1960, 849–852.
J. Am. Chem. Soc. 82, 6070-4 (1960).
J. Org. Chemistry, 26, 3628-31 (1961).
J. Med. Chem. 1970 13(2), 169-76.
Tetrahedron 1977, 33(10) 1219-26.
J. Prakt. Chem. 1977 319(6), 927-33.
Z. Naturforsch, B: Anorg, Chem., Org. Chem., 1979 34B(10) 1434-42.
Z. Naturforsch, B: Anorg. Chem., Org. Chem., 1980, 35(C)(1–2), 49-56.
Z. Naturforsch, B: Anorg. Chem., Org. Chem, 1983, 38(B) 392-97.

*Primary Examiner*—Richard L. Raymond
*Assistant Examiner*—Mark W. Russell
*Attorney, Agent, or Firm*—Annette Moore; Carol J. Roth; Tom M. Moran

[57] ABSTRACT

Naphthalenes of the formula:

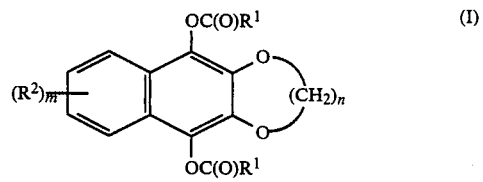

wherein:
m is 1 or 2;
n is 1, 2, or 3;
$R^1$ is alkyl of one to seven carbon atoms or an optionally substituted phenyl;
$R^2$ is hydrogen, lower alkyl, lower alkoxy, optionally substituted phenyl, optionally substituted phenyl-lower-alkyl, optionally substituted phenyl-lower-alkoxy, amino, lower alkylamino, lower dialkylamino, halo, cyano, hydroxy, or lower alkylthio are useful in relieving psoriasis.

28 Claims, No Drawings

NAPHTHALENE ANTI-PSORIATIC AGENTS

BACKGROUND OF THE INVENTION

1. Field of the Invention

The invention relates to naphthalene derivatives which are useful in inhibiting certain dermatological conditions. This invention also relates to pharmaceutical compositions useful in relieving the effects of certain chronic recurrent papulosquamous dermatoses, e.g., psoriasis. This invention also relates to a process for preparing compounds of this invention.

2. Related Disclosures

Psoriasis is a skin disease characterized in part by excessive proliferation of cells of the epidermis which remain strongly adherent and build up into a scaley plaque typical of the disease. While currently available therapies, such as corticosteroids, vitamin A derivatives (retinoids) cancer chemotherapeutic agents (methotrexate, razoxane), coal tar and anthralin preparations, and psoralen-u.v. irradiation (PUVA) are effective in controlling the disease to a certain extent, they can cause numerous and sometimes severe undesirable side effects including renal irritation, hepatic toxicity, and erythema.

Certain 2,3-methylenedioxy-4,9-naphthoquinones are known but no useful biological activity has been ascribed to them. See Z. Naturforsch., B: Anorg Chem., Org. Chem. 1983, 383(3), 392-7. Certain naphthoquinones and esters thereof are known to be useful in treating psoriasis. See, for example, U.S. Pat. Nos. 4,229,478, 4,466,981 and 4,593,120 and British Pat. No. 1,243,401. Surprisingly, it has been discovered that the compounds of the instant invention are also effective antipsoriatic agents.

SUMMARY

The present invention relates to compounds of the formula

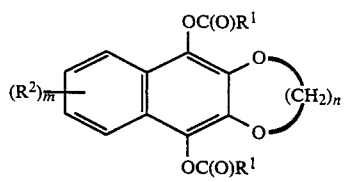

wherein:
m is 1 or 2;
n is 1, 2 or 3;
$R^1$ is alkyl of one to seven carbon atoms or an optionally substituted phenyl; and
$R^2$ is hydrogen, lower alkyl of one to six carbon atoms, lower alkoxy of one to six carbon atoms, optionally substituted phenyl, optionally substituted phenyl-lower-alkyl, optionally substituted phenyl-lower-alkoxy, amino, lower alkylamino, lower dialkylamino, halo, hydroxy, or lower alkylthio.

Another aspect of the invention is a pharmaceutical composition in a form suitable for topical adminstration to mammals comprising a compound of formula (I) and a pharmaceutically acceptable excipient.

Another aspect of the invention is a method for relieving the condition of psoriasis in a mammal which comprises topically administering to said mammal a psoriasis-relieving amount of a compound of formula (I).

Yet another aspect of the invention is preparing compounds of formula (I) by reacting compounds of formula (VIII)(infra) with an acylating agent such as an acid anhydride.

DETAILED DESCRIPTION AND PREFERRED EMBODIMENT

In its broadest aspect, the present invention relates to the compounds of the following formula

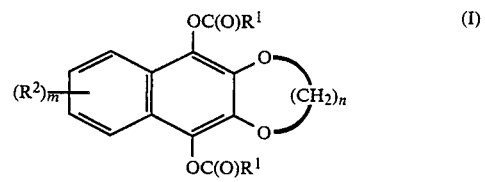

wherein:
m is 1 or 2;
n is 1, 2 or 3;
$R^1$ is alkyl of one to seven carbon atoms or an optionally substituted phenyl; and
$R^2$ is hydrogen, lower alkyl of one to six carbon atoms, lower alkoxy of one to six carbon atoms, optionally substituted phenyl, optionally substituted phenyl-lower-alkyl, optionally substituted phenyl-lower-alkoxy, amino, lower alkylamino, lower dialkylamino, halo, cyano, hydroxy, or lower alkylthio.

A preferred group of compounds of formula (I) are those wherein both $R^1$'s are the same and are lower alkyl of one to five carbon atoms. Within this group it is preferred that n is 1 or 2.

A more preferred group of compounds of formula (I) are those wherein both $R^1$'s are methyl. It is also preferred that n is 1.

Another preferred group of compounds of formula (I) are those wherein $R^2$ is hydrogen, bromo, chloro, fluoro, cyano, lower alkyl or lower alkoxy. It is preferred that m is 1 and that substitution is in the 6-position and is hydrogen or chloro.

In the present specification and claims the term "alkyl" is intended to mean alkyl groups containing one to seven carbon atoms including straight chain groups, or branched chain groups. Illustrative of such groups are for example, methyl, ethyl, n-propyl, i-propyl, n-hexyl, 2-methylpentyl, and n-heptyl. The term "lower alkyl" refers to alkyl groups of one to six carbon atoms as defined above. Examples of "lower alkyl" groups are methyl, ethyl, n-propyl, i-propyl, n-butyl, i-butyl, s-butyl, 2,2-dimethylpropyl and t-hexyl.

The term "optionally substituted phenyl-lower-alkyl" refers to an optionally substituted phenyl ring attached to an alkylene chain of one to six carbon atoms. Examples of "optionally substituted phenyl-lower-alkyl" are benzyl, 4-chlorobenzyl, 2-methylphenylethyl and phenyl-n-propyl.

The term "lower alkoxy" refers to a straight or branched chain saturated aliphatic group of one to six carbon atoms having bonded thereto an oxygen moiety. Examples of "lower alkoxy" are methoxy, ethoxy, n-propoxy, i-propoxy, n-butoxy, i-butoxy, s-butoxy, t-butoxy and n-pentyloxy.

"Optionally substituted phenyl-lower-alkoxy" refers to a phenyl ring attached to an alkylene chain of one to six carbon atoms having bonded thereto an oxygen atom. Examples of "optionally substituted phenyl-lower-alkoxy" are benzyloxy, 4-chlorophenylethoxy and phenyl-n-propoxy.

The term "lower alkylthio" refers to a saturated straight or branched chain aliphatic group of one to six carbon atoms having bonded thereto a sulfur moiety. Examples of "lower alkylthio" are methylthio, ethylthio, n-propylthio, i-butylthio and n-hexylthio.

"Optionally substituted phenyl" refers to a phenyl ring optionally substituted by one or more substituents selected from the group consisting of lower alkyl, lower alkoxy, halo, lower acyl, lower acyloxy, cyano, nitro, amino and lower acylamino.

The term "halo" refers to fluoro, chloro, and bromo. The term "cyano" refers to the group —CN. The term "amino" refers to the group —NH$_2$.

The term "lower alkylamino" refers to an amino group substituted by lower alkyl as is defined above. Examples of "lower alkylamino" are methylamino, ethylamino and n-butylamino.

The term "lower dialkylamino" refers to an amino group substituted by two lower alkyl groups. Examples of "lower dialkylamino" are dimethylamino, dipropylamino and methylethylamino.

The term "lower acyl" refers to the group $R^3C(O)$- wherein $R^3$ is a lower alkyl group of one to six carbon atoms or an optionally substituted phenyl group. Examples of "lower acyl" are acetyl, propanoyl, butanoyl and benzoyl.

The term "lower acyloxy" refers to the group $R^3C(O)O$- wherein $R^3$ is defined above.

The term "lower acylamino" refers to the group $R^3C(O)NH$- wherein $R^3$ is as defined above.

The nomenclature used in naming the compounds of the invention will consider the dioxy ring as a substituent at the 2 and 3 position of the naphthalene ring. The numbering of the ring is represented below:

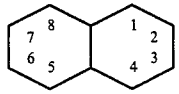

For example, the compound of the following structure is named as 6-chloro-2,3-ethylenedioxy-1,4-diacetyloxynaphthalene.

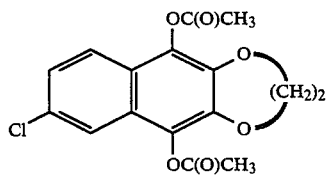

FORMULATION AND ADMINISTRATION

The compositions of the present invention may be formulated for administration in any convenient way by analogy with other topical compositions adapted for use in mammals. These compositions may be presented for use in any conventional manner with the aid of any of a wide variety of pharmaceutical carriers or vehicles.

The naphthalenes of formula (I) may be formulated with suitable pharmaceutical vehicles known in the art to form particularly effective topical compositions. An effective amount of the naphthalene compound is about 0.001% w to about 10% w of the total formulated composition. The rest of the formulated composition will be about 90% w to about 99.999% w of a suitable excipient which may include a pharmaceutically acceptable solvent and other pharmaceutically acceptable additives to form a topically effective pharmaceutical formulation.

A pharmaceutically acceptable solvent is one which is substantially non-toxic and non-irritating under the conditions used and may be readily formulated into any of the classical drug formulations such as powders, creams, ointments, lotions, gels, foams, aerosols, solutions and the like. Particularly suitable solvents include water, ethanol, acetone, glycerine, propylene carbonate, dimethylsulfoxide (DMSO), and glycols such as 1,2-propylene diol, i.e., propylene glycol, 1,3-propylene diol, polyethylene glycol having a molecular weight of from 100 to 10,000, dipropylene glycol, etc. and mixtures of the aforementioned solvents with each other.

A topical cream may be prepared as a semi-solid emulsion of oil in water or water in oil. A cream base formulation by definition is an emulsion, which is a two-phase system with one liquid (for example fats or oils) being dispersed as small globules in another substance (e.g., a glycol-water solvent phase) which may be employed as the primary solvent for the naphthalenes therein. The cream formulation may contain fatty alcohols, surfactants, mineral oil or petrolatum and other typical pharmaceutical adjuvants such as anti-oxidants, antiseptics, or compatible adjuvants. A typical cream base formulation is as follows:

| | |
|---|---|
| Water/glycol mixture (15% or more glycol) | 50–99 parts by weight |
| Fatty Alcohol | 1–20 |
| Non-ionic Surfactant | 0–10 |
| Mineral Oil | 0–10 |
| Typical Pharmaceutical Adjuvants | 0–5 |
| Active Ingredients | 0.001–10 |

The fatty alcohol, non-ionic surfactant, and other adjuvants are discussed in U.S. Pat. No. 3,934,013 to Poulsen which is incorporated herein by reference.

The naphthalenes of formula (I) may also be formulated as topical ointments. A "classical" ointment is a semisolid anhydrous composition which may contain mineral oil, white petrolatum, a suitable solvent such as a glycol and may include propylene carbonate and other pharmaceutically suitable additives such as surfactants, for example Span and Tween, or wool fat (lanolin), along with stabilizers such as antioxidants and other adjuvants as mentioned before. Following is an example of a typical "classical" ointment base:

| | |
|---|---|
| White Petrolatum | 40–94 parts by weight |
| Mineral Oil | 5–20 |
| Glycol Solvent | 1–15 |
| Surfactant | 0–10 |
| Stabilizer | 0–10 |
| Active Ingredients | 0.001–10.0 |

Other suitable ointment base formulations which employ propylene carbonate are described in U.S. Pat. No. 4,017,615 issued Apr. 12, 1977 by Shastri et al entitled "Propylene Carbonate Ointment Vehicle" and U.S. Pat. No. 3,924,004 issued Dec. 2, 1975 by Chang et al entitled "Fatty Alcohol-Propylene Carbonate-Glycol Solvent Cream Vehicle". As much of those applications as is pertinent is incorporated herein by reference. Following is a typical ointment base formulation containing propylene carbonate:

| Active Ingredients | 0.001–10.0 parts by weight |
|---|---|
| Propylene Carbonate | 1–10 |
| Solvent | 1–10 |
| Surfactant | 0–10 |
| White Petrolatum | 70–97 |

Suitable solvents, surfactants, stabilizers, etc. are discussed in U.S. Pat. No. 3,934,013 and such are incorporated herein by reference.

A suitable topical "non-classical" anhydrous, water washable "ointment type" base is described in U.S. Pat. No. 3,592,930 to Katz and Neiman, and that patent is incorporated herein by reference. A representative composition of this invention utilizing such base is as follows:

| Glycol Solvent | 40–35 parts by weight |
|---|---|
| Fatty Alcohol | 15–45 |
| Compatible Plasticizer | 0–15 |
| Compatible Coupling Agent | 0–15 |
| Penetrant | 0–20 |
| Active Ingredients | 0.001–10.0 |

Another aspect of the invention is a method for relieving the condition of psoriasis in a mammal by topically administering a composition containing a compound of formula (I). Generally, the anti-psoriatic manifestation in mammals, particularly humans, is combatted by contacting the inflamed areas with a therapeutically effective amount of the naphthalene-containing compositions of this invention, that is, an amount which results in a lessening of the epidermal cell proliferation (an anti-psoriatic effect). Preferably the naphthalenes are first formulated to prepare a suitable pharmaceutical formulation, as discussed herein above, which is then placed in contact with the afflicted area(s). An effective amount of the naphthalene compound will depend upon the particular condition and the mammal receiving the treatment and will vary between 0.001% to 10% by weight of the pharmaceutical composition and preferably will be between 0.01% and 1% by weight of the formulation. Using these levels in the formulation, a therapeutically effective and non-side effect producing amount, i.e. enough to affect an anti-psoriatic response, but not enough to adversely effect the recipient, is applied to the afflicted area(s).

The compounds of this invention are also useful for treating mammals having a variety of disease states caused by lipoxygenase activity, particularly 5-lipoxygenase activity.

In vitro lipoxygenase inhibiting activity of the compounds of this invention are determined by the standard Human Polymorphonuclear Leukocytes assay. This assay is a modification of that described by O. Radmark, C. Malmsten, and B. Samuelsson in *FEBS Letter*, 110, 213–215, 1980. In vivo lipoxygenase inhibiting activity of the compounds of this invention are determined by the arachidonic acid mouse ear inflammation assay as described by J. M. Young, D. A. Spires, C. J. Bedord, B. Wagner S. J. Ballaron and L. M. DeYoung in *Journal of Investigative Dermatology*, 82, 367–371, 1984.

PREPARATION

The compounds of formula (Va) and (Vb) which are intermediates for compounds of formula (VI) may be prepared according to Reaction Sequence A shown below.

REACTION SEQUENCE A

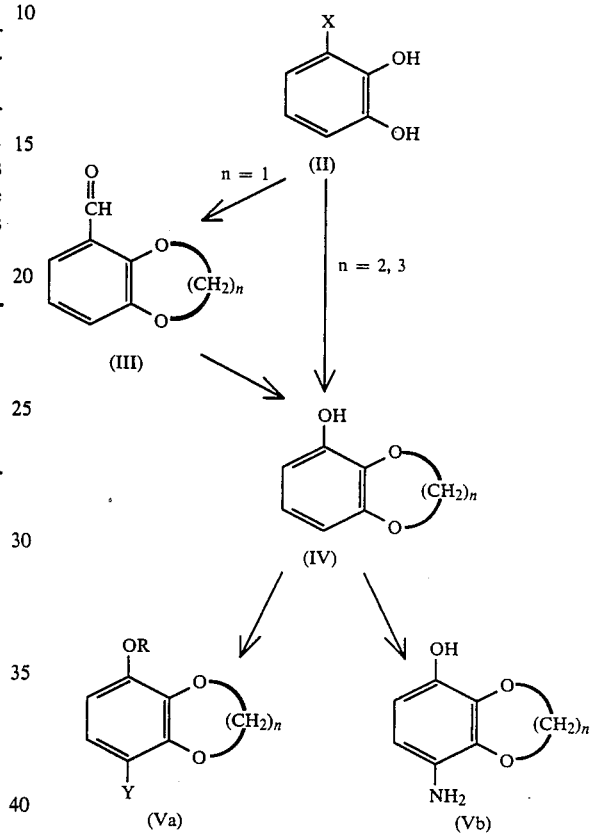

wherein n is 1, 2 or 3 and X and Y are independently formyl, formate, hydroxy or hydrogen.

Compound of formula (III) is prepared by reacting a dibromo-n-alkane of one to three carbon atoms with compound of formula (II).

When n is 1, compound of formula (II) wherein X is formyl, i.e., 2,3-dihydroxybenzaldehyde, is reacted with dibromomethane by forming a mixture of the aldehyde, dibromomethane, an alkali metal carbonate such as potassium carbonate and a catalyst such as copper (II) oxide in a solvent such as dimethylformamide, N-methylpyrrolidone and the like. The mixture is heated at reflux for 1 to 6 hours, preferably for 2 to 6 hours. The reaction mixture is then cooled and compound of formula (III) wherein X is formyl is recovered by, e.g., evaporation followed by aqueous extraction.

Compound of formula (III) is converted to compound of formula (IV) wherein n is 1 by the Bayer-Villiger oxidation which comprises oxidizing the formyl group with an organic peracid such as m-chloroperbenzoic acid (mCPBA) or performic acid (generated in situ by the addition of hydrogen peroxide to formic acid) to a formate ester group. The formate ester group is hydrolyzed to the corresponding phenol with a base such as sodium hydroxide, potassium hydroxide and the like to give the compound of formula (IV) wherein n is 1.

The hydroxy of the phenol of formula (IV) where n is 1 is protected with benzyl by treating with a benzyl halide, preferably benzyl bromide, in the presence of a base, such as potassium carbonate or 1,5-diazobicyclo[5.4.0]undec-5ene (DBU), to form compound of formula (Va) where R is benzyl and Y is hydrogen. Treatment of the compound of formula (Va) where n is 1 with excess N-methylformanilide and phosphorus oxychloride in chlorobenzene at temperatures from −20° C. to ambient, preferably at −5° C., yields a mixture of formylation products. Compound of formula (Va) where R is benzyl and Y is formyl is isolated by evaporation followed by aqueous extraction and chromatography over silica gel. Compound of formula (Va) where R is benzyl and Y is formyl is oxidized by the Bayer-Villiger oxidation described above to the compound of formula (Va) where Y is the formate ester. The formate of formula (Va) is hydrolyzed with aqueous base, as described above, to yield the phenol of formula (Va) where R is benzyl and Y is hydroxy. Hydrogenolysis of the benzyl protecting group using palladium-on-carbon as catalyst in a solvent such as tetrahydrofuran or the like gives the hydroquinone, compound of formula (Va) where R is hydrogen and Y is hydroxy. The hydroquinone is oxidized with transition metal salts such as cuprous chloride, ferrous chloride or ceric ammonium nitrate, preferably ceric ammonium nitrate, in mixtures of water and miscible organic solvents, preferably acetonitrile, to form compound of formula (VI), infra, where n is 1.

When n is 2 or 3, compound of formula (IV) is prepared directly from compound of formula (II) wherein X is hydroxy, i.e., pyrogallol, by reacting with 1,2-dibromoethane (n is 2) or 1,3-dibromopropane (n is 3). Pyrogallol in a suspension with alkali metal carbonate such as potassium carbonate in a solvent such as dimethylformamide, N-methylpyrrolidone and the like is heated to 60° to 120° C., preferably at 60° to 100° C. for ½ to 4 hours, preferably for 1 to 3 hours. The dibromo compound is then added over a 2 to 6 hour period, preferably over a 3 to 5 hour period. The resulting mixture is stirred at 60° C. to 120° C., preferably at 60° C. to 100° C. for 2 to 24 hours, preferably for 3 to 4 hours. After cooling the mixture, compound of formula (IV) wherein n is 2 or 3 is recovered by e.g. extraction and evaporation.

2,3-Dihydroxybenzaldehyde and pyrogallol are commercially available from i.e., Aldrich Chemical Co.

Compound of formula (IV) wherein n is 2 or 3 is converted to compound of formula (Vb) by first diazotizing sulfanilic acid with sodium nitrite under reaction conditions well known in the art for diazo reactions. The diazo compound formed is coupled with compound of formula (IV) at 0° to 15° C., preferably at 10° C.

The coupled compound is cleaved by a reducing agent such as sodium dithionite (sodium hyposulfite). The reducing agent is added to the coupled compound dissolved in water basified with a base such as sodium hydroxide at room temperature. The solution is cooled to 0° to 10° C. and the pH is adjusted to 7 with a concentrated acid such as concentrated hydrochloric acid. The resulting solution is extracted with a solvent such as dichloromethane and compound of formula (Vb) is recovered by evaporation.

Compound of formula (Vb) is dissolved in a cold solution of aqueous sulfuric acid and a chilled solution of an oxidizing agent such as sodium dichromate and the like is slowly added. After extraction of the solution with a solvent such as dichloromethane compound of formula (VI), infra, wherein n is 2 or 3 is recovered by evaporation.

Compounds of formula (VII) may be prepared by Reaction Sequence B which is shown below:

REACTION SEQUENCE B

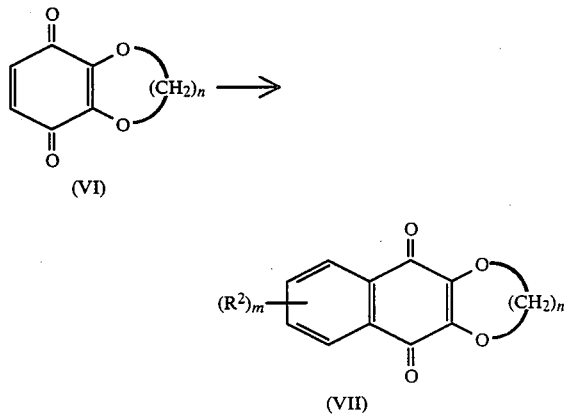

wherein $R^1$, $R^2$, m and n as defined above.

Compound of formula (VII) is prepared by reacting the benzoquinone of formula (VI) wherein n is 1, 2 or 3 with an optionally substituted butadiene in a solvent such as acetic acid at −10° C. to 30° C., preferably at 25° C. for 24 to 72 hours, preferably from 40 to 48 hours. The 5,8-dihydro precursor of the compound of formula (VII) is recovered and treated with an oxidizing agent such as sodium dichromate, sodium nitrate and the like. Compound of formula (VII) is recovered by procipitation from water.

The reagents, 2-chloro-1,3-butadiene (choroprene), 2-methyl-1,3-butadiene (isoprene), 2-ethyl-1,3-butadiene, 1-methoxy-1,3-butadiene, 1-phenyl-1,3-butadiene and 2-phenyl-1,3-butadiene and the like are available from, i.a., Pfaltz and Bauer Chemical Co. 2-Bromo-1,3-butadiene and 2-fluoro-1,3-butadiene may be prepared by methods well known in the art, for example, by the methods discussed in J. Am. Chem. Soc., 55 786 (1933) and U.S. Pat. No. 2,401,850, respectively.

Alternatively, compounds of formula (VII) wherein n is 2 or 3 may be prepared from compound of formula (IX) according to Reaction Sequence C shown below.

REACTION SEQUENCE C

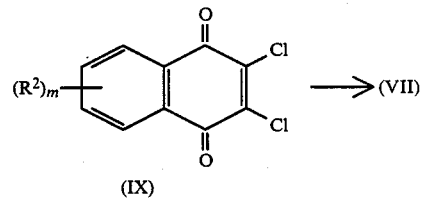

wherein $R^2$ and m are as defined above.

2,3-Dichloronaphthoquinone is treated with a solution preapared from equivalents of metallic sodium in a diol of the formula $HO(CH_2)_nOH$ where n is 2 or 3, at temperatures from ambient to 100° C., preferably 60° C., for from 30 minutes to 16 hours, preferably 2 hours, to form the intermediate of formula (VII).

Compound of formula (IX) is prepared by reacting a butadiene substituted with the appropriate embodiment of $R^2$ with 1,4-benzoquinone in a solvent such as acetic acid at a temperature of $-10°$ C. to $30°$ C., preferably at $25°$ C. for 24 to 72 hours, preferably from 40 to 48 hours. The 5,8-dihydro derivative is recovered and treated with an oxidizing agent such as sodium dichromate, sodium nitrate, manganese dioxide and the like to form the substituted 1,4-naphthoquine. Compound of formula (IX) is prepared by reacting the 1,4-naphthoquinone with chlorine gas. The chlorine gas is bubbled into a solution of the naphthoquinone dissolved in a solvent such as glacial acetic acid, nitrobenzene, carbon tetrachloride and the like, preferably glacial acetic acid at reflux temperature in the presence of a suitable catalyst such as sodium acetate, iodine, iron(III) chloride, dimethylformamide or lower alcohols.

The compound of formula (IX) wherein $R^2$ is hydrogen is commercially available from, i. a. Aldrich Chemical Co.

Another method for preparing compound of formula (VII) is set out in Reaction Sequence D.

REACTION SEQUENCE D

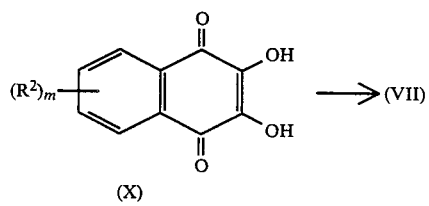

Compound of formula (X) is treated with two equivalents of a strong base, such as DBU, potassium t-butoxide or sodium hydride, preferably sodium hydride, in a polar aprotic solvent such as dimethylformamide, tetrahydrofuran, preferably dimethylformamide. A 1,n-dibromoalkane such as dibromomethane, 1,2-dibromoethane and 1,3-dibromopropane is slowly added to the reaction mixture to form the intermediate of formula (VII).

Compound of formula (X) may be prepared by the process discolsed in U.S. Pat. No. 4,229,478 incorporated herein by reference.

Compounds of formula (I) are prepared from compounds of formula (VII) by first hydrogenating to form compounds of formula (VIII)

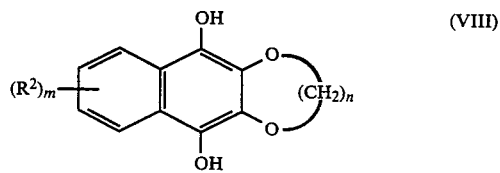

at atmospheric pressure in the presence of a catalyst such as palladium-on-carbon and then reacting the hydrogenated compound with an acylating agent and pyridine such as alkanoyl anhydride, optionally substituted benzoic anhydride, for example, acetic anhydride, benzoic anhydride and the like in a solvent such as tetrahydrofuran, diethyl ether and the like. After ½ to 3 hours, preferably after ½ to 1½ hours compounds of formula (I) are recovered by recrystallization.

The following specific description is given to enable those skilled in the art to more clearly understand and practice the present invention. It should not be considered as a limitation upon the scope of the invention but merely as illustrative and representative thereof.

PREPARATION 1

2,3-Methylenedioxybenzaldehyde (Compound of Formula (III) where X=formyl and n=1)

A mixture containing 2,3-dihydroxybenzaldehyde, (50 g) dibromomethane (188 g), potassium carbonate (150 g) and copper (II) oxide (1.4 g) in dimethylformamide (2 L) was heated at reflux for 4 hours. The reaction mixture was cooled, filtered and evaporated. The residue was dissolved in toluene and the organic layer was washed with staturated sodium bicarbonate and brine. The layer was then dried, filtered and evaporated to yield 46.5 g of 2,3-methylenedioxybenzaldehyde mp $32°-33°$ C.

PREPARATION 2

2,3-methylenedioxyphenol (Compound of Formula (IV) where n=1)

2,3-Methylenedioxybenzaldehyde (46.5 g) was dissolved in dichloromethane, and to it was added mCPBA (80 g) in small portions. The resulting solution was brought to reflux overnight, then cooled and evaported. The residue was dissolved in ethyl acetate, and the organic layer was washed with saturated sodium bicarbonate, and was then dried, filtered and evaporated to afford 56 g of the crude formate. The intermediate was dissolved in methanol (50 mL) and 10% aqueous potassium hydroxide (180 mL) was added. After 1 hour, the solution was acidified with concentrated hydrochloric acid and extracted with ether. The organic phase was washed with brine. It was then dried, filtered and evaporated to give 30.8 g of 2,3-methylenedioxyphenol crystallized from dichloromethane-hexane, mp $62°-63°$ C.

PREPARATION 3

2,3-Ethylenedioxyphenol (Compound of Formula (IV) where n=2)

A suspension of pyrogallol (126 g) and potassium carbonate (138 g) in dimethylformamide (500 mL) was stirred at $80°$ C. for 2 hours. 1,2-Dibromoethane (188 g) was then added dropwise over a 4 hour period and the resulting mixture was stirred at $80°$ C. overnight. Upon cooling, the mixture was filtered, and the filtrate was evaporated, dissolved in water (200 mL) and acidified with concentrated hydrochloric acid. The resulting mixture was extracted with toluene. The orgainc extract was washed with water, dried over sodium sulfate, filtered and evaporated. Fractional distillation ($82°$ C., 0.05 mm) afforded 54.7 g of 2,6-ethylenedioxyphenol, as an oil. Similary, using the above procedure but substituting 1,3-dibromopropane for 1,2-dibromoethane 2,3-propylenedioxyphenol, mp $110°-111°$ C. was prepared.

PREPARATION 4

1-Benzyloxy-2,3-Methylenedioxybenzene (Compound of Formula (Va) where R=benzyl and Y=H A solution of 2,3-methylenedioxyphenol (17.45g) and benzyl bromide (27.5 mL) in dimethylformamide (200 ml) was treated with potassium carbonate (35 g), and the mixture was heated at 60° C. overnight. After cooling and filtering, the mixture was evaporated. The residue was dissolved in ethyl acetate and washed with 1 M hydrochloric acid. The organic extract was dried, filtered and evaporated to afford 1-benzyloxy-2,3-methylenedioxybenzene, mp 62°–63° C.

PREPARATION 5

4-Benzyloxy-2,3-Methylenedioxybenzaldehyde (Compound of Formula (Va) where R=benzyl and Y=formyl)

1-Benzyloxy-2,3-methylenedioxybenzene (47.8 g) in chlorobenzene (50 ml) was added dropwise to a mixture of N-methylformanilide (34 g) and phosphorus oxychloride (38.5 g) in chlorobenzene (50 ml) maintained at −5° C. When the addition was complete the reaction mixture was allowed to warm to room temperature. It was then poured onto ice, and stirred overnight. The resulting mixture was extracted with ethyl acetate, washed with water and brine, and then dried and evaporated to yield 47.9 g of crude product as an isomeric mixture of aldehydes. Silica gel chromatography using 1:1 dichloromethane-hexane afforded 7 g of 4-benzyloxy-2,3-methylenedioxybenzaldehyde, mp 81°–82° C.

PREPARATION 6

4-Benzyloxy-2,3-Methylenedioxyphenol (Compound of Formula (Va) where R=benzyl and Y=OH)

Solid mCPDA (6.74 g) was added portionwise to a chilled solution of 4-benzyloxy-2,3-methylenedioxybenzaldehyde (8.35 g) in dichloromethane (150 ml). After stirring at room temperature overnight, the mixture was evaporated, dissolved in ethyl acetate and washed with saturated aqueous sodium bicarbonate, water and brine. The organic extract was dried, filtered and evaporated, and the residue was dissolved in methanol. The solution was treated with 10% aqueous potassium hydroxide to remove the formate group. Upon acidification, 4-benzyloxy-2,3methylenedioxyphenol was isolated as a solid and used directly in Preparation 7.

PREPARATION 7

2,3-Methylenedioxy-1,4-Benzoquinone (Compound of Formula (VI) where n=1)

A solution of 4-benzyloxy-2,3-methylenedioxyphenol (7.7 g) in tetrahydrofuran (50 ml) was hydrogenated at atmospheric pressure over palladium-on-carbon overnight. The catalyst was removed by filtration, and the resulting hydroquinone intermediate was oxidized in actonitrile solution with ceric ammonium nitrate (25 g). After 5 minutes the reaction was quenched with water and extracted with ethyl acetate. Evaporation of the organic extract and chromatography afforded 4.9 g of 2,3-methylenedioxy-1,4-benzoquinone, mp 106°–7° C.

PREPARATION 8

2,3-Ethylenedioxy-1,4-Benzoquinone (Compound of Formula (VI) where n=2)

To a mechanically stirred suspension of sulfanilic acid (45.7 g) and sodium nitrite (18.9 g) in water (250 ml) cooled to 10° C. was added concentrated HCl (45 ml) dropwise. The resulting solution was stirred for 1 hour at 10° C., and then was added over 1 hour to a stirred mixture of phenol (40 g) and sodium hydroxide (54 g) in water (330 mL). The resulting mixture was stirred 1 hour at 10° C., and was then allowed to warm to ambient temperature with stirring overnight. The solution was acidified with concentrated HCl and the resulting precipitate of azo compound was collected by filtration. The azo compound was dissolved in a solution of sodium hydroxide (46 g) in water (1 L) blanketed under nitrogen, and to it was added sodium dithionite (125 g). The resulting light yellow solution was cooled to 0°–10° C. and was adjusted to pH 7 with concentrated HCl. After filtration to remove particulate matter, the solution was extracted with dichloromethane. The organic extract was dried, filtered and evaporated to yield 33 g of crude aminophenol. The aminophenol was dissolved in a cold solution of aqueous sulfuric acid (90 mL in 200 mL water) and to it was slowly added a chilled solution of sodium dichromate (105 g) in water (1 L). The solution was exhaustively extacted with dichlormethane to afford 14.6 g of 2,3-ethylenedioxy-1,4-benzoquinone, mp 156° C.

Similarly using the above procedure but substituting the appropriate aminophenol for 2,3-ethylenedioxy-4-aminophenol the following compound is prepared: 2,3-propylenedioxy-1,4-benzoquinone.

PREPARATION 9

6-Chloro-2,3-Ethylenedioxy-1,4-Naphthoquinone (Compound of Formula (VII) where $R^2$=Cl, m=1 and n=2)

A mixture of 2,3-ethylenedioxy-1,4-benzoquinone (17 g) and freshly distilled chloroprene (13 g) in glacial acetic acid (100 mL) was stirred at ambient temperature for 90 hours. The mixture was then diluted with additional acetic acid (500 mL) followed by the addition of a solution of sodium dichromate (40 g) and sulfuric acid (2 mL) in water (25 mL). The mixture was heated at 60° –70°C. for 2 hours, then cooled and diluted with water (500 mL). The resulting bright orange precipitate was collected and dried to yield 18.25 g of 6-chloro-2,3-ethylenedioxy-1,4-naphthoquinone, mp 279°–80° C.

Similarly, using the above procedure but substituing the appropriate reactants the following compounds are prepared:
6-chloro-2,3-propyleneioxy-1,4-naphthoquinone, mp. 209°–210° C.;
6-chloro-2,3-methylenedioxy-1,4-naphthoquinone, mp. 235°–236° C.;
2,3-ethylenedioxy-1,4-naphthoquinone;
2,3-methylenedioxy-1,4-naphthoquinone;
2,3-porylenedioxy-1,4-naphthoquinone;
6-bromo-2,3-ethylenedioxy-1,4-naphthoquinone;
6-fluoro-2,3-methylenedioxy-1,4naphthoquinone;
5-chloro-2,3-propylenedioxy-1,4-naphthoquinone;
5-cyano-2,3-ethylenedioxy-1,4-naphthoquinone;
6-cyano-2,3-methylenedioxy-1,4-naphthoquinone;
6-methylamio-2,3propylenedioxy-1,4-naphthoquinone;
6-diethylamino-2,3-ethylenedioxy-1,4-naphthoquinone;
6-ethylmethylamino-2,3-methylenedioxy -1,4-naphthoquinone;
6-methoxy-2,3-propylenedioxy-1,4-naphthoquinone;
6-ethoxy-2,3-ethylenedioxy-1,4-naphthoquinone;
6butoxy-2,3-methylenedioxy-1,4-naphthoquinone;
6-phenylethoxy-2,3-propylenedioxy-1,4-naphthoquinone;
6-methyl-2,3-ethylenedioxy-1,4-naphthoquinone;

6-i-propyl-2,3-methylenedioxy-1,4naphthoquinone;
6-phenyl-2,3-propylenedioxy-1,4napthoquinone;
6-benzyl-2,3-ethylenedioxy-1,4-naphthoquinone;
5-chloro-2,3-methylenedioxy-1,4naphthoquinone;
5-chloro-2,3-propylenedioxy-1,4naphthoquinone;
5-chloro-2,3-ethylenedioxy-1,4naphthoquinone;
6,7-dichloro-2,3-methylenedioxy-1,4-naphthoquinone;
6,7- dimethyl-2,3propylenedioxy-1,4napthoquinone;
6-(2-chlorophenyl) -2,3ethylenedioxy-1,4-naphthoquinone;
6hydroxy-2,3methylenedioxy-1,4-naphthoquinone;
6-methylthio-2,3-propylenedioxy-1,4-naphthoquinone; and
6-i-propylthio-2,3-ethylenedioxy-1,4naphthoquinone.

PREPARATION 10

6-Chloro-2,3-ethylenedioxy-1,4-naphthoquinone

Compound of Formula (VII) where $R^2$=Cl, m=1 and n=2)

2,3,6-Trichloronaphthoquinone (13.1 g) is added in small portions to a solution previously prepared from ethylene glycol (500 ml) and sodium metal (2.3 g) and heated to 80° C. under nitrogen. Upon completion of the addition, the reaction mixture is diluted with water (1 L) and cooled. The resulting precipitate is collected to afford 6-chloro-2,3-ethylenedioxy-1,4-naphthoquinone as an orange solid.

PREPARATION 11

6-Choloro-2,3-Ethylenedioxy-1,4Naphthoquinone (Compound of Formula (VII) where $R^2$=Cl, m=1 and n=2)

6-Chloro-2,3-dihydroxy-1,4-naphthoquinone (11.25 g) dissolved in dry dimethylformamide (100 ml) is treated with washed sodium hydride (2.64 g) in small portions under a blanket of nitrogen. After stirring 1 hour at room temperature, 1,2-dibromoethane (4.3 ml) is added via a syringe over 1 hour. The resultant mixture is warmed to 60° C. overnight, then cooled and diluted with water (500 ml) to afford 6-chloro-2,3-ethylenedioxy-1,4-naphthoquinone.

EXAMPLE I

6-Chloro-2,3-Ethylenedioxy-1,4-Diacetyloxynaphthalene (Compound of Formula (I) where $R^2$=methyl, $R^2$=Cl, m=1 and n=2).

A supension of 6-chloro-2,3-ethylenedioxy-1,4-naphthoquinone (2 g) in tetrahydrofuran was hydrogenated at 1 atm over 10% palladium-on-carbon (0.5 g). When the solution was colorless, a solution of acetic anhydride (4 g), pyridine (3.16 g) and 4-dimethylaminopyridine (0.2 g) in tetrahydrofuran (25 mL) was added. After 1 hour, the solution was filtered and evaporated, and the resdiue was dissolved in dichloromethane. The organic layer was washed with 1 M hydrcholoric acid and brine and then dried. The dried layer was filtered and evaported. Crystallization from ether gave 1.20 g of 6-chloro-2,3-ethylenedioxy-1,4-diacetyloxynaphthlene, mp 179°-180° C.

Similarly, using the appropriate reactants in the above procedure the following compounds are prepared:
2,3-ethylenedioxy-1,4-diacetyloxynaphthalene;
2,3-methylenedioxy1,4-diacetyloxynaphthalene;
2,3-propylenedioxy1,4-diacetyloxynaphthalene;
6-cholor-2,3-ethylenedioxy-1,4-di-n-propxyanoyloxynaphthalene, mp 131°-2° C.;
6-chloro-2,3-methylenedioxy-1,4-di-i-butanoylyoxynaphthalene;
6-chloro-2,3-propylenedioxy-1,4-di(2,2-dimethylpropanoyloxy)naphthlene, mp 156°-7° C.;
6-chloro-2,3-ethylenedioxy-1,4-di-n-octanoyloxynaphthalene;
6-cholor-2,3-methylenedioxy-1,4-diacetyloxynaphthalene, mp 126°-7° C.;
6-chloro-2,3-propylenedioxy-1,4-diacetyloxynaphthalene, mp 136°-7° C.
2,3-ethylenedioxy-1,4-di-n-petanoyloxynaphthalene;
6-chloro-2,3-methylenedioxy-1,4-dipropanoyloxynaphthalene, mp 138°-9° C.;
6-chloro-2,3-propylenedioxy-1,4-dioctanoyloxynaphthalene;
6-chloro-2,3-methylenedioxy-1,4-di-(2,2-dimethypropanoyloxy)naphthalene, mp 189°-90° C.;
6-chloro-2,3-methylenedioxy-1,4-dibenzoyloxynaphthalene, mp 200°-1° C.;
6-chloro-2,3-ethylenedioxy-1,4-di(2,2-dimethylpropanoyloxy)naphthalene, mp 152°-3° C.;
6-chloro-2,3ethylenedioxy-1,4-di(2-methylpropanoloxy)naphthalene, mp 105°-6° C.;
6-chloro-2,3-ethylenedioxy-1,4-dibutanoyloxynaphthalene, mp 108°-9° C.;
6-chloro-2,3ethylenedioxy-1,4-dibenzoyloxynaphthalene, mp 199°-200° C.;
6-chloro-2,3-propylenedioxy-1,4-dipropanoyloxynaphthalene, mp 113°-4° C.;
6-chloro-2,3-propylenedioxy-1,4-dibutanoyloxynaphthalene, mp 59°-60° C.;
6-chloro-2,3-propylenedioxy-1,4(2-methylpropanoloxy)naphthalene, mp 106°-7° C.;
6-chloro-2,3-propylenedioxy-1,4-dibenzoyloxynaphthalene, mp 183°-4° C.;
6-bromo-2,3-ethylenedioxy-1,4-diacetyloxynaphthalene;
6-fluoro-2,3-methylenedioxy-1,4-diacetyloxynaphthalene;
5-cyano-2,3-ethylenedioxy-1,4diacetyloxynaphthalene;
6-cyano-2,3-methylenedioxy-1,4-diacetyloxynaphthalene;
6-methylamino-2,3-propylenedioxyl-1,4-diacetyloxynaphthalene;
6-diethylamino-2,3-ethylenedioxy-1,4-dipropanoyloxynaphthalene;
6-ethylmethylamino-2,3-methylenedioxy-1,4-di-n-butanoyloxynaphthalene;
6-methoxy-2,3-propylenedioxy-1,4-di-n-pentanoyloxynaphthalene;
6-ethoxy-2,3-ethylenedioxy-1,4-di-n-hexanoyloxynaphthalene;
6-i-butoxy-2,3methylenedioxy-1,4-di(2,2-dimethylpropanoyloxy)naphthalene;
6-phenylethoxy-2,3propylenedioxy-1,4-diacetyloxynaphthalene;
6-methyl-2,3-ethylenedioxy-1,4diacetyloxynaphthalene;
6-i-propyl-2,3-methylenedioxy-1,4-di-n-octanoylomynaphthalene;
6-phenyl-2,3-propylenedioxy-1,4-diacetyloxynaphthalene;
6-benzyl-2,3-ethylenedioxy-1,4-dipropanoyloxynaphthalene;

5-chloro-2,3-methylenedioxy-1,4-di-n-butanoylox-ynaphthalene;
5-chloro-2,3-propylenedioxy-1,4-diacetyloxynaphthalene;
5-chloro-2,3-ethylenedioxy-1,4-di-n-octanoyloxynaphthalene;
5-chloro-2,3-methylenedioxy-1,4-diacetyloxynaphthalene;
2,3-ethylenedioxy-1,4-di-n-propanoyloxynaphthalene;
2,3-methylenedioxy-1,4-di-i-butanoyloxynaphthalene;
2,3-propylenedioxy-1,4-di-n-pentanoyloxynaphthalene;
2,3-ethylenedioxy-1,4-di(2,2-dimethylpropanoyloxy)-naphthalene;
2,3-methylenedioxy-1,4-di-n-propanoyloxynaphthalene;
6,7-dichloro-2,3-methylenedioxy-1,4-di-n-heptanoyloxynaphthalene;
6,7-dimethyl-2,3-propylenedioxy-1,4-di(4-chlorobenzoyloxy)naphthalene:
6-(2-chlorophenyl)-2,3-ethylenedioxy-1,4diacetyloxynaphthalene;
6-hydroxy-2,3-methylenedioxy-1,4-diacetyloxynaphthalene;
6-methylthio-2,3-propylenedioxy-1,4-di(2-methoxybenzoyloxy)naphthalene; and
6-i-propylthio-2,3-ethylenedioxy-1,4-diacetyloxynaphthalene.

What is claimed is:

1. A compound of the formula

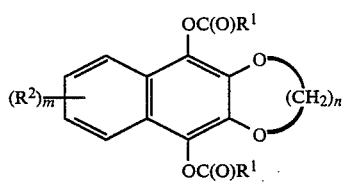 (I)

wherein:
m is 1 or 2;
n is 1, 2 or 3;
$R^1$ is alkyl of one to seven carbon atoms or an optionally substituted phenyl; and
$R^2$ is hydrogen, lower alkyl of one to six carbon atoms, lower alkoxy of one to six carbon atoms, optionally substituted phenyl, optionally substituted phenyl-lower-alkyl, optionally substituted phenyl-lower-alkoxy, amino, lower alkylamino, lower dialkylamino, halo, cyano, hydroxy, or lower alkylthio.

2. The compound of claim 1 wherein $R^2$ is hydrogen, lower alkyl of one to six carbon atoms, lower alkoxy of one to six carbon atoms, optionally substituted phenyl, optionally substituted phenyl-lower-alkyl, optionally substituted phenyl-lower-alkoxy, halo, cyano, or lower alkylthio.

3. The compound of claim 2 wherein $R^2$ is hydrogen, halo, cyano, lower alkyl of one to six carbon atoms or lower alkoxy of one to six carbon atoms.

4. The compound of claim 3 wherein $R^1$ is lower alkyl of one to five carbon atoms or phenyl.

5. The compound of claim 4 wherein n is 1.

6. The compound of claim 5 wherein $R^1$ is methyl, $R^2$ is hydrogen and m is 1, which is 2,3-methylenedioxy-1,4-diacetyloxynaphthalene.

7. The compound of claim 5 wherein $R^1$ is methyl, $R^2$ is chloro and m is 1, which is 6-chloro-2,3-methylenedioxy-1,4-diacetyloxynaphthalene.

8. The compound of claim 5 wherein $R^1$ is t-butyl, $R^2$ is chloro and m is 1, which is 6-chloro-2,3-methylenedioxy-1,4di(2,2-dimethylpropanoyloxy)naphthalene.

9. The compound of claim 5 wherein $R^1$ is ethyl, $R^2$ is chloro and m is 1, which is 6-chloro-2,3-methylenedioxy-1,4-dipropanoyloxynaphthalene.

10. The compound of claim 5 wherein $R^1$ is phenyl, $R^2$ is chloro and m is 1, which is 6-chloro 2,3-methylenedioxy-1,4-dibenzoyloxynaphthalene.

11. The compound of claim 4 wherein n is 2.

12. The compound of claim 11 wherein $R^1$ is methyl, $R^2$ is hydrogen and m is 1, which is 2,3-ethylenedioxy-1,4-diacetyloxynaphthalene.

13. The compound of claim 11 wherein $R^1$ is methyl, $R^2$ is chloro and m is 1, which is 6-chloro-2,3-ethlenedioxy-1,4-diacetyloxynaphthalene.

14. The compound of claim 11 wherein $R^1$ is t-butyl, $R^2$ is chloro and m is 1, which is 6-chloro-2,3-ethylenedioxy-1,4-di(2,2-dimethylpropanoyloxy)naphthalene.

15. The compound of claim 11 wherein $R^1$ is i-propyl, $R^2$ is chloro and m is 1, which is 6-chloro -2,3-ethylenedioxy-1,4-di(2-methylpropanoyloxynaphthalene.

16. The compound of claim 11 wherein $R^1$ is n-propyl, $R^2$ is chloro and m is 1, which is 6-chloro-2,3-ethylenedioxy-1,4-di-n-butanoyloxynaphthalene.

17. The compound of claim 11 wherein $R^1$ is phenyl, $R^2$ is chloro and m is 1, which is 6-chloro-2,3-ethylenedioxy-1,4dibenzyloxynaphthalene.

18. The compound of claim 4 wherein n is 3.

19. The compound of claim 18 wherein $R^1$ is methyl, $R^2$ is hydrogen and m is 1, which is 2,3-propylenedioxy-1,4-diacetyloxynaphthalene.

20. The compound of claim 18 wherein $R^1$ is methyl, $R^2$ is chloro and m is 1 which is 6-chloro-2,3-propylenedioxy-1,4-diacetyloxynaphthalene.

21. The compound of claim 18 wherein $R^1$ is t-butyl, $R^2$ is chloro and m is 1, which is 6-chloro-2,3-propylenedioxyl-1,4-di(2,2dimethylpropanoyloxy)-naphthalene.

22. The compound of claim 18 wherein $R^1$ is ethyl, $R^2$ is chloro and m is 1, which is 6-chloro-2,3-propylenedioxy-1,4-dipropanoyloxynaphthalene.

23. The compound of claim 18 wherein $R^1$ is n-propyl, $R^2$ is chloro and m is 1, which is 6-chloro-2,3-propylenedioxy-1,4-dibutanoyloxynaphthalene.

24. The compound of claim 18 wherein $R^1$ is i-propyl, $R^2$ is chloro and m is 1, which is 6-chloro-2,3-propylenedioxy-1,4-di(2-methylpropanoyloxynaphthalene.

25. The compound of claim 18 wherein $R^1$ is phenyl, $R^2$ is chloro and m is 1, which is 6-chloro-2,3-propylenedioxyl-1,4-dibenzoyloxynaphthalene.

26. The compound of claim 1 wherein $R^2$ is hydrogen or chloro and is in the 6-position.

27. A pharmaceutical composition in a form for topical administration for relieving psoriasis which composition comprises an effective amount of a compound of claim 1 and a pharmaceutically acceptable excepient.

28. A method of treating a mammal having psoriasis which method comprises applying to the mammal an effective amount of a compound of claim 1.

* * * * *